(12) United States Patent
Lowe et al.

(10) Patent No.: US 9,848,959 B2
(45) Date of Patent: Dec. 26, 2017

(54) MASSAGING OR BRUSHING BITE PLATES

(71) Applicant: ORTHOACCEL TECHNOLOGIES, INC., Bellaire, TX (US)

(72) Inventors: Michael K. Lowe, Bellaire, TX (US); Zaffer Syed, Bellaire, TX (US); Tamsen Valoir, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 244 days.

(21) Appl. No.: 14/292,354

(22) Filed: May 30, 2014

(65) Prior Publication Data

US 2014/0272761 A1   Sep. 18, 2014

Related U.S. Application Data

(63) Continuation-in-part of application No. 11/773,849, filed on Jul. 5, 2007, now Pat. No. 9,668,828.

(Continued)

(51) Int. Cl.
| | | |
|---|---|---|
| *A61C 7/00* | (2006.01) | |
| *A61C 17/22* | (2006.01) | |
| *A61C 7/08* | (2006.01) | |
| *A61C 17/20* | (2006.01) | |
| *A61C 19/06* | (2006.01) | |

(Continued)

(52) U.S. Cl.
CPC ............. *A61C 7/008* (2013.01); *A46B 9/025* (2013.01); *A46B 9/045* (2013.01); *A61C 7/00* (2013.01); *A61C 7/08* (2013.01); *A61C 17/005* (2013.01); *A61C 17/0211* (2013.01); *A61C 17/16* (2013.01); *A61C 17/20* (2013.01); *A61C 17/22* (2013.01); *A61C 17/228* (2013.01); *A61C 17/3481* (2013.01); *A61C 19/063* (2013.01); *A61H 13/00* (2013.01); *A61N 5/0603* (2013.01); *A61C 7/002* (2013.01); *A61H 2201/0207* (2013.01); *A61H 2201/10* (2013.01); *A61N 2005/0606* (2013.01); *A61N 2005/067* (2013.01); *A61N 2005/0651* (2013.01); *A61N 2005/0659* (2013.01); *A61N 2005/0661* (2013.01)

(58) Field of Classification Search
CPC ......... A61C 7/008; A61C 17/228; A61C 7/08; A61C 17/20
USPC ........................................ 433/2, 24, 80, 215
See application file for complete search history.

(56) References Cited

U.S. PATENT DOCUMENTS 4,164,940 A * 8/1979 Quinby .................. A61H 13/00
                                                    433/216
4,237,574 A * 12/1980 Kelly ..................... A46B 9/045
                                                    15/167.2

(Continued)

FOREIGN PATENT DOCUMENTS

| DE | 19934117 | 8/2000 |
|---|---|---|
| WO | 2009123965 | 3/2008 |
| WO | 2012088250 | 6/2012 |

OTHER PUBLICATIONS

Kau, et al., The clinical evaluation of a novel cyclical force generating device in orthodontics, Orthodontic Practice 1(1) (2010).

*Primary Examiner* — Nicholas Lucchesi
(74) *Attorney, Agent, or Firm* — Boulware & Valoir

(57) ABSTRACT

An orthodontic remodeling device, wherein the bite plate is modified to have textured teeth and gum facing surfaces so as to provide cleaning, massaging or acupressure effect when in use.

22 Claims, 10 Drawing Sheets

Related U.S. Application Data

(60) Provisional application No. 61/837,021, filed on Jun. 19, 2013, provisional application No. 61/911,355, filed on Dec. 3, 2013.

(51) Int. Cl.

| | | |
|---|---|---|
| A61C 17/00 | (2006.01) | |
| A61C 17/02 | (2006.01) | |
| A61C 17/16 | (2006.01) | |
| A46B 9/02 | (2006.01) | |
| A46B 9/04 | (2006.01) | |
| A61C 17/34 | (2006.01) | |
| A61H 13/00 | (2006.01) | |
| A61N 5/06 | (2006.01) | |
| A61N 5/067 | (2006.01) | |

(56) References Cited

U.S. PATENT DOCUMENTS

| | | | |
|---|---|---|---|
| 4,348,178 A | 9/1982 | Kurtz | |
| 4,372,004 A | 2/1983 | Vermillion | |
| 4,411,625 A | 10/1983 | Koblitz | |
| 4,459,193 A | 7/1984 | Ratcliffe | |
| 4,771,084 A | 9/1988 | Kubota | |
| 5,017,626 A | 5/1991 | Tomura | |
| 5,030,098 A | 7/1991 | Branford | |
| 5,165,761 A | 11/1992 | Dirksing | |
| 5,325,560 A | 7/1994 | Pavone | |
| 5,365,624 A * | 11/1994 | Berns | A61C 17/0211 15/22.1 |
| 5,518,300 A | 5/1996 | Meyer | |
| 5,542,749 A | 8/1996 | Toth | |
| 5,605,383 A | 2/1997 | Biocca | |
| 5,636,988 A * | 6/1997 | Murayama | A61C 15/047 433/118 |
| 5,856,373 A | 1/1999 | Kaisaki | |
| 5,926,904 A | 7/1999 | Warner | |
| 5,967,784 A | 10/1999 | Powers | |
| 6,161,243 A | 12/2000 | Weihrauch | |
| 6,341,824 B1 | 1/2002 | Boucherie | |
| 6,353,956 B1 | 3/2002 | Berge | |
| 6,405,401 B1 | 6/2002 | Hellerud | |
| 6,648,639 B2 * | 11/2003 | Mao | A61C 7/22 433/18 |
| 6,869,148 B2 | 3/2005 | Stein | |
| 6,871,373 B2 | 3/2005 | Driesen | |
| 6,988,777 B2 | 1/2006 | Pfenniger | |
| 7,044,737 B2 * | 5/2006 | Fu | A61C 17/20 433/119 |
| 7,661,430 B2 * | 2/2010 | Mason | A62B 9/06 128/848 |
| 8,241,035 B2 * | 8/2012 | Jones | A61C 17/20 433/29 |
| 8,308,246 B2 | 11/2012 | Chung | |
| 8,500,446 B2 * | 8/2013 | Lowe | A61C 7/00 433/18 |
| 9,028,250 B2 * | 5/2015 | Spaulding | A61C 7/00 433/147 |
| 2004/0241620 A1 * | 12/2004 | Allred | A61C 5/00 433/215 |
| 2005/0049326 A1 | 3/2005 | Park | |
| 2006/0225235 A1 * | 10/2006 | Mortimer | A46B 5/0012 15/167.2 |
| 2007/0009856 A1 * | 1/2007 | Jones | A61C 17/20 433/215 |
| 2008/0227046 A1 | 9/2008 | Lowe | |
| 2008/0227047 A1 | 9/2008 | Lowe | |
| 2010/0043165 A1 | 2/2010 | Juentgen | |
| 2010/0055634 A1 * | 3/2010 | Spaulding | A61C 7/00 433/5 |
| 2010/0062397 A1 | 3/2010 | Brewer | |
| 2011/0136070 A1 * | 6/2011 | Rubin | A61C 7/008 433/2 |
| 2011/0200973 A1 | 8/2011 | Rawls | |
| 2012/0090118 A1 | 4/2012 | Lambertson | |
| 2012/0260442 A1 | 10/2012 | Thompson | |
| 2012/0317738 A1 | 12/2012 | Birk | |
| 2012/0322018 A1 | 12/2012 | Lowe | |
| 2013/0059263 A1 | 3/2013 | Lowe | |
| 2013/0192012 A1 | 8/2013 | Paciullo | |

* cited by examiner

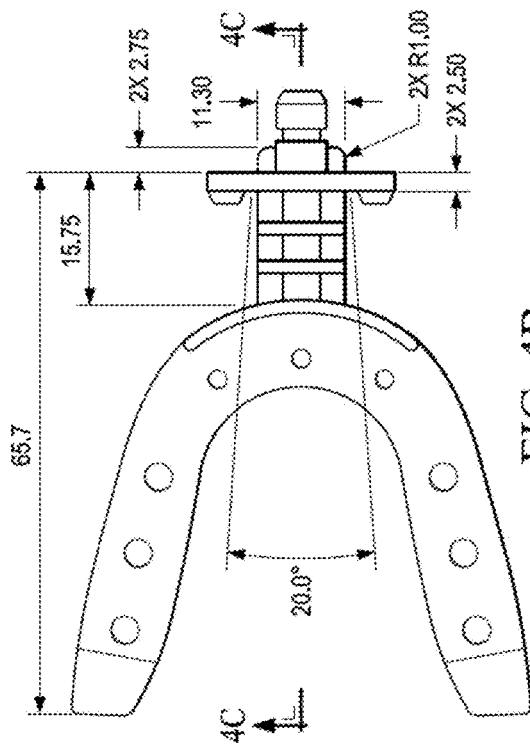
FIG. 4B
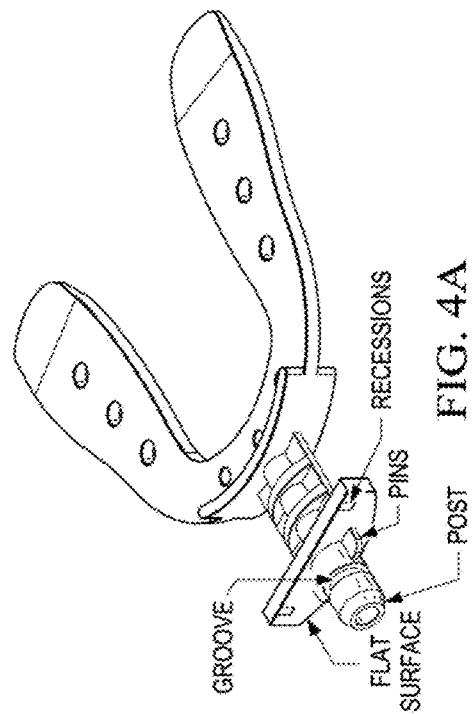
FIG. 4A
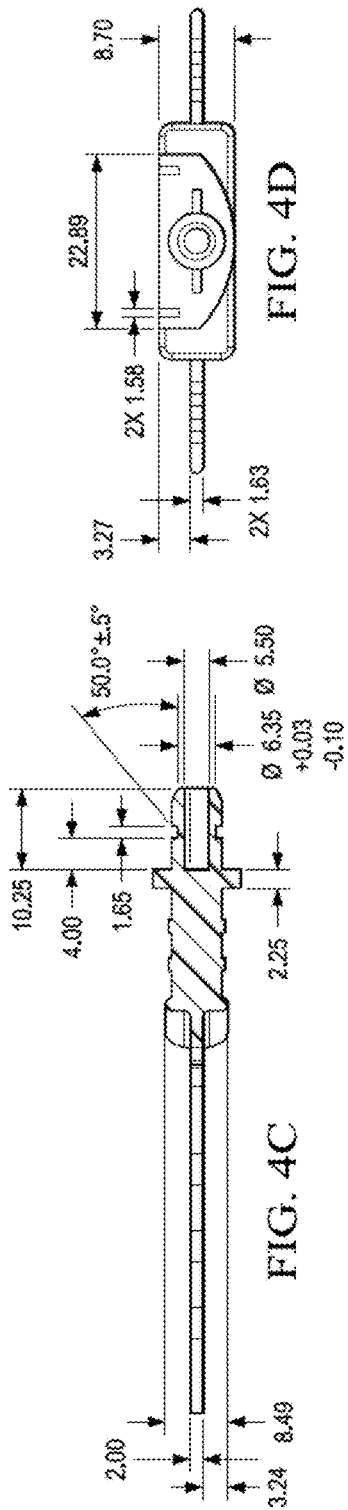
FIG. 4D
FIG. 4C

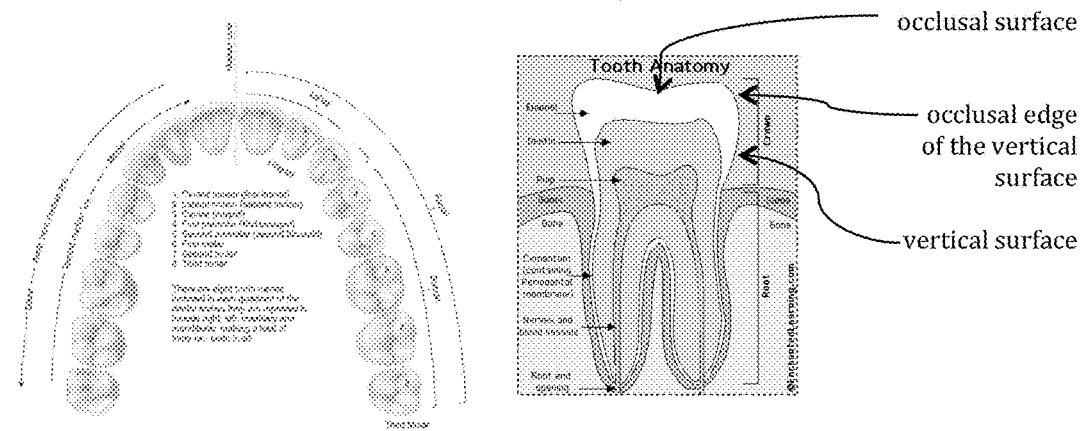

MASSAGING OR BRUSHING BITE PLATES

PRIOR RELATED APPLICATIONS

This application is a continuation-in-part of U.S. Ser. No. 11/773,849, filed Jul. 5, 2007. This invention claims priority to U.S. Ser. No. 61/837,021, titled MASSAGING BITE PLATE and filed on Jun. 19, 2013. It also claims priority to 61/911,355, titled BRUSHING BITE PLATE and filed on Dec. 3, 2013. Each application is expressly incorporated by reference herein in its entirety for all purposes.

FIELD OF THE DISCLOSURE

The invention relates to biteplates for use with various orthodontic remodeling devices, especially vibratory devices, wherein the bite plate has a textured inner surface so as to massage the gums while in use or a bristled bite plate so as to clean teeth and braces while in use.

BACKGROUND OF THE DISCLOSURE

A malocclusion is a misalignment of teeth or incorrect relation between the teeth of the two dental arches. According to Edward Angle, "father of modern orthodontics," the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom are a malocclusion.

Orthodontics, formerly orthodontia (from Greek orthos "straight or proper or perfect"; and odous "tooth"), is the specialty concerned with the study and treatment of malocclusion, which can be a result of tooth irregularity, disproportionate facial skeleton relationship, or both. Orthodontics treats malocclusion through the displacement of teeth via bony remodeling and control and modification of facial growth. Simply put, pressure is applied to teeth, and the high pressure side results in bone loss (osteoclastic activity), whereas the low pressure side produces bone growth (osteoblastic). The socket holding the tooth thus gradually shifts position, moving the tooth along with it.

This process has been accomplished for hundreds of years using static mechanical force to induce bone remodeling, thereby enabling teeth to move. In modern orthodontics, braces consisting of an archwire interfaces with brackets that are affixed to each tooth. As the teeth respond to the pressure applied via the archwire by shifting their positions, the wires are again tightened to apply additional pressure. This widely accepted approach to treating malocclusion takes about twenty-four months on average to complete, and is used to treat a number of different classifications of clinical malocclusion.

Treatment with braces is complicated by the fact that it is uncomfortable and/or painful for patients, and the orthodontic appliances are perceived as unaesthetic, all of which creates considerable resistance to use. Additionally, the 24-month treatment time is very long, and further reduces usage. In fact, some estimates provide that less than half of the patients who could benefit from such treatment elect to pursue orthodontics. However, until recently, no method was available to speed orthodontic remodeling since increasing force only increases tooth resorption, and is thus contraindicated.

Cyclic forces have been proposed to speed orthodontic remodeling, but Mao was probably the first to show faster bone growth under vibration in a rabbit model. The early Mao studies provided a basis for both possible efficacy and likely safety for using vibration in humans to assist orthodontic tooth movement, but the Mao studies used rabbit cranial clamp and suture closure experiments. Therefore, a device suitable for human clinical work still had to be developed and tested.

OrthoAccel Technologies Inc., invented the first commercially successful orthodontic vibrating device, as described in US2008227046 and related cases, designed to apply cyclic forces to the dentition for accelerated remodeling purposes. Both intra-oral and extraoral embodiments are described in US2008227046, each having processors to capture and transmit patient usage information, which is an important tool in ensuring compliance. The bite plate was specially designed to contact occlusal as well as facial and/or lingual surfaces of the dentition, and thus was more effective than any prior art devices in conveying vibrational forces to the teeth. Additionally, the device was slim, capable of hands free operation, lacked the bulky head gear of the prior art devices, and had optimized force and frequency for alveolar bone remodeling. Thus, its comfort level and compliance was also found to be high, with patients reporting that they liked the device, especially after the motor was redesigned to be quieter and smoother, as described in US2010055634 et seq. In fact, this device has been marketed as AcceleDent® in the United States, and several other countries and has achieved remarkable commercial success since its recent introduction. AcceleDent® represents the first successful clinical approach to accelerate orthodontic tooth movement by modulating bone biology in a non-invasive and non-pharmacological manner. The device was tested in clinical trials and shown to speed orthodontic remodeling as much as 50% (Kau 2010).

A common side effect of using braces is the appearance of white spot lesions, uncovered when the braces are finally removed. These unsightly spots are a unwelcome sight for any teenager or young adult who wore painful braces for two to four years to improve their smile, only to have their teeth marred by chalky white spots at the end.

The earliest sign of a new carious lesion is the appearance of a chalky white spot on the surface of the tooth, indicating an area of demineralization of enamel. This is referred to as a white spot lesion, an incipient carious lesion or a "microcavity". The formation of white spot lesions or enamel demineralization around fixed orthodontic attachments is a common complication during and following fixed orthodontic treatment, and mars the result of a successfully completed case.

Demineralization is an almost inevitable side-effect associated with fixed orthodontic appliance treatment, especially when associated with poor oral hygiene. The acidic byproducts of the bacteria in plaque are responsible for the subsequent enamel demineralization and formation of white spot lesions. These can cause caries thereby leading to poor esthetics, patient dissatisfaction and legal complications. The formation of white spot lesions after completion of orthodontic therapy is discouraging to a specialty, one of whose goals is to improve aesthetics in the dento-facial region.

White spot lesions develop in association with brackets, bands, arch wires, ligatures and other orthodontic devices that complicate conventional oral hygiene measures, leading to prolonged plaque accumulation. This concern raises the need for assessing the saliva, oral hygiene status and caries rate before beginning of treatment and initiating preventive measures. Orthodontists must take up the active responsibility to educate patients about the importance of maintaining good dietary compliance and excellent oral hygiene regime.

Clinically, formation of white spots around orthodontic attachments can occur as early as 4 weeks into treatment and their prevalence among orthodontic patients ranges from 2% to 96%. The labio-gingival area of the lateral incisors is the most common site for white spot lesions and the maxillary posterior segments are the least common site, with males affected more in comparison with females. One clinical study found that a sharp increase in the number of white spot lesions occurred during the first 6 months of treatment that continued to rise at a slower rate to 12 months, thus in initial months of the treatment critical evaluation of oral hygiene is recommended.

A method of improving hygiene of braces is thus critically needed. One method would be to design a whole-mouth toothbrush, such that braces, teeth and gums can be simultaneously cleaned.

US20120260442 describes a whole-mouth electric toothbrush that is U-shaped and has a plurality of rotating bristle heads thereon. However, this device is complex and would be expensive to manufacture, and in addition, the bristles are not optimized for use with braces or other fixed orthodontic appliances. To date, no commercial embodiment of such a device is available, probably reflecting the complexity of driving a plurality of rotating heads at a distance from motor components.

U.S. Pat. No. 6,353,956 describes an ultrasonic whole-mouth toothbrush that has bristles on the bite tray contacting all occlusal and vertical teeth surfaces. Thus, the point of contact with the teeth is the relatively soft bristles and very little vibration will be conveyed to the teeth and underlying bone. Further, the frequency used therein was ultrasonic, which has not yet been demonstrated to have any accelerative effect on tooth movement.

A simpler, non-vibrational whole-mouth tooth brush has become recently available. The BLIZZIDENT is made by 3D scanning. The cost is quite high, but is expected to decrease as 3D scanning costs continue to decrease. However, this device is not made to clean fixed orthodontic appliances, and requires manual activation by e.g., chewing action, to move the bristles.

What is needed in the art is a method of improving oral health, circulation, hygiene of braces, and the like. A method or device that takes advantage of the existing vibrational driver would be particularly useful, as providing additional functionality for the already cleared FDA device. This application addresses some of those improvements.

SUMMARY OF THE DISCLOSURE

The invention is directed to a massaging and/or brushing bite plates, that can preferably be used with the existing extraoral vibrational driver, and thus reduce the incidence of white spot lesions by virtue of improving hygiene.

One embodiment provides a bite plate with bristles specially designed to clean braces and the tooth surfaces near braces. The occlusal bristles can be omitted, or if included be short and/or stiff and/or dense enough to adequately convey the vibrational forces to the teeth and bone, thus increasing osteoclastic/osteoblastic activity and speeding orthodontic remodeling as proven in clinical trials. The use of shorter stiffer bristles in this area will not cause difficulty because there is no soft tissue here to abrade. Further, even if omitted entirely, this is not expected to present difficulty, since white spots lesions do not typically appear on occlusal surfaces and normal brushing will suffice for these surfaces. The bristles can also be combined with massaging projections, e.g., in the gum area thus improving circulation and further improving oral health.

Another embodiment is a massaging bite plate that has a textured surface on the uppermost and lowermost edges of the inner lingual and buccal rims, such that the texture contacts the gums, thus massaging same while in use. Preferably, the texture comprises small rubber fingers, with some distance therebetween, so as provide an acupressure and/or massaging effect.

The fingers-like projections should have rounded tips where intended to be used with a vibratory device, as such will provide a comfortable massaging effect. However, a less rounded and more pointed tip can be used where an acupressure effect is intended, and vibration is either omitted or reduced in force so as to accommodate the pointier tips.

The bite plates provided herein will provide hygiene and periodontal health benefits, stimulating blood flow to the area, and the brace bristles serving a brace/tooth cleaning effect. In fact, soft massaging projections can be provided to the gum area, and a stiffer, finer bristle be provided for the brace/tooth area, thus optimizing the cleaning effect, especially those areas around the braces, where hygiene is always difficult. Alternatively, the longer massaging tips can have shorter fine bristles therebetween, thus massaging the gum and cleaning brace surfaces. This embodiment will allow both functions, regardless of the size of the crown surfaces, which can vary significantly between individuals.

The bite plate preferably has an inner core that is made of e.g., metal, a resin such as polyacrylate, or ceramic, and serves to provide support for connection to extraoral remodeling devices, such as the vibrator, IR or micropulse devices. However, if the bite plate materials are otherwise strong enough for reversible connection to a driver, the inner core can be omitted. In yet other embodiments, the inner core can comprise all needed functionality, such as vibrators, batteries, activation switches, LEDs, and the like.

In bite plates for vibration treatment modalities, the core is flat and sufficiently stiff so as to transmit vibration to the mouthpiece and thence to the teeth. Further, the bristles and/or textured surfaces should not impede the transfer of vibration to the teeth and bone either.

If desired, additional coatings can be applied thereto, e.g., a soft, tasteless coating can be provided over an otherwise suitable material that has unpleasant taste. Silicone is known to provide a material with the desired characteristics, but additional polymers are known, and some are described below. Alternatively, the coating can be a fluoride releasing material, as described in 61/769,507, filed Feb. 26, 2013.

The bite plate can be combined with any other treatment modality, including vibration, laser light, IR light, electromagnetic pulses, electrical micropulses, heat, and the like. However, the bite plate is preferably used with the existing extraoral vibrational device, which is already cleared for marketing in the US and several other places and already has proven efficacy. In addition, the same principles can be applied to a completely intra-oral device, wherein the vibratory source or other treatment modality, power source and wiring are mounted directly on the bite plate.

The bite plate can be assembled using the inner core, which is generally U-shaped to contact the occlusal surfaces of the Euro arch (e.g., narrowing as it progresses from the posterior (molar) to the anterior (incisor) teeth. If intraoral, the components are placed on the inner core, then the entire assembly is covered with the polymeric covering, thus hermetically sealing the components against water ingress.

The bite plate also has a vertical edge (aka rim or phalange) to contact at least one of the facial and lingual surfaces, especially for a vibrational treatment modality, as this allows the vibration to be in an up-and-down direction via the occlusal contact, as well as front-to-back direction via facial rim contact. The vertical edges thus allow the vibration to be transferred to the teeth in two axes and are much preferred over a simple flat bite plate. The edges also serve to keep the bite plate correctly positioned over the teeth, and provide the surface that can be used for massaging, acupressure, or dental cleaning effect.

In a massaging embodiment, since massaging is directed towards the gums, such embodiments need a higher rim than the prior art models, which had no need to contact the gums. Further, the bite plate can have rims on both facial and lingual sides, thus massaging both the facial/exterior and lingual/interior gum surfaces.

However, for a cleaning modality, bristles should be opposite the dentition, and thus, the rims could be lower if the gum massaging modality is omitted. As above, the bristles can be both exterior and on interior surfaces, thus cleaning front and back of teeth, or the bristles can be only on the facial rims, since many patients have braces on the front, and this is where the cleaning effect is needed. For those patients being treated with lingual braces or other fixed lingual appliances, this would obviously be reversed.

The preferred polymer for the bite plate has no taste or toxicity, does not leach components such as plasticizers (except where intended to release active agents such as fluoride), and is preferably tested for same before use according to known tests. Where a polymer does leach, it can be coated with a sealant, but a non-leaching polymer is preferred since sealants have a limited lifespan in an oral environment.

The most preferred materials are medical grade or FDA cleared for oral use and are tasteless, non-toxic, and biocompatible. Suitable resins may include an epoxy, a cyanoacrylate, an acrylate, a urethane, an acrylate and urethane mixture, a urethane oligomer/(meth)acrylate monomer blend resin, a silicone, a silicone copolymer, or a copolymer of hydrogen siloxanes and unsaturated compounds. Silicone is particularly preferred.

Alternatively, the resin may comprise copolymers of hydrogen siloxanes and unsaturated compounds. These may be used as adhesion promoters to build a chemical link between the resin and the inner core. An example of such an adhesive is described in DE19934117 and incorporated by reference herein for all purposes. Other resins are described in e.g., U.S. Pat. No. 5,856,373; 2011/0200973; U.S. Pat. No. 5,017,626; U.S. Pat. No. 4,459,193; U.S. Pat. No. 4,411,625; U.S. Pat. No. 4,771,084; US20050049326.

Preferred polymers are clear, but colored pellets can be added to the polymer in the molten form, this making colored bite plates, which can appeal to younger patients. If desired, the outer surfaces can also be imprinted with designs, and if needed for longevity can be coated with a sealant.

Bristle shape, size and arrangement are well known in the art, as well as methods of gathering and setting tufts or bristles by staple-set technology, fusion technology, in-mold technology, and the like. For example, U.S. Pat. No. 6,871,373, U.S. Pat. No. 6,161,243 U.S. Pat. No. 6,405,401, U.S. Pat. No. 5,325,560 describe various bristles, shapes and patterns suitable for toothbrush use. US20100043165, U.S. Pat. No. 5,518,300, U.S. Pat. No. 6,869,148 describes various tuft or bristle fixation methods and/or machines for same. US20120090118 describes angling tufts. U.S. Pat. No. 5,926,904 U.S. Pat. No. 4,372,004 describes tufts made on twisted wire, e.g., as in a bottlebrush.

U.S. Pat. No. 5,165,761, for example, teaches how to make a multi-length bristle brush by attaching all of the bristle tufts of the shortest overall length followed by cutting and end rounding of the individual bristles in the first group of tufts while all of the free ends of the bristles are in a first plane. This is done prior to affixing the next group of bristle tufts of greater overall length. The cutting and end rounding sequence is thereafter repeated for each ascending bristle tuft elevation. The final toothbrush bristle contour is a function of the pattern of attachment for each bristle tuft elevation.

U.S. Pat. No. 8,308,246 describes collecting a plurality of bristles substantially close together and fusing and subsequently hardening ends of the collected bristles to each other by cutting to thereby fuse the ends of the collected bristles using a heated cutter to thus produce a bundle of bristles. U.S. Pat. No. 6,341,824 describes another method of making such tufts.

U.S. Pat. No. 6,988,777 describes a toothbrush with a head part and at least one carrier element which is connected thereto and has a plurality of cutouts through which bristle filaments are guided and, for fastening on the carrier element, are melted by way of their buried ends.

In the conventional manufacturing process for brushes, particularly toothbrushes, the brushes are injection molded with empty tuft holes in the toothbrush head, and of course tuft holes can be placed at different angles. The tuft holes may also be drilled after the injection molding. In a secondary operation, U shaped tufts of bristles are inserted into the holes in the head. Each tuft of bristles is held in place by a plate-like staple that is wider than the tuft hole so that when the staple is used to drive the U-shaped bristle tufts into the tuft hole, the edges of the staple slightly cut and deform the sides of the hole. The pressure and resulting static friction of the surrounding plastic on the staple contributes to forces maintaining the staple in place. Alternatively, tufts can be secured with adhesives or heat-sealed, or any other method can be used.

Toothbrush staples of the rectangular type have become available in which at least one of the major surfaces thereof is provided with parallel horizontal grooves (i.e., grooves that extend parallel with a longitudinal axis of the staple), thereby yielding a staple that has been found to be more resistant to becoming separated from its tuft hole than staples with smooth surfaces. US20130192012 describes a staple with a specially designed topography that provides reliable anchoring and creation from cost effective materials.

Staples are not always used however, and there are many other methods of fixing tufts to a tuft carrier. US20120317738 describes a tuft making method wherein tufts are embedded at one of their ends at least partially in a bristle carrier, wherein the ends are fused by heat before embedding, wherein different amounts of heat are supplied to each of the at least two different cleaning elements. U.S. Pat. No. 5,542,749 describes another tuft making method.

Inserting tufts into holes or slots is just one method of making bristles, although it is most commonly used for toothbrushes. Another method is to place bristles between two wires, and then twist the wires, trapping and twisting the bristle to form a bottlebrush. In bottlebrushes, the bristles can be very regularly spaced around the 360° circumference or more irregularly positioned, as desired. U.S. Pat. No. 5,605,383 describes one such method. A 360° bristle range is easily converted to 180° by adhesion or otherwise attaching the backbone to a surface which forces bristles to bend.

A removable bristle head can be provided with this method if the ends of the wires snap fit or otherwise reversible attach to the bite plate. This is particularly useful since the wire brush can be made separately and frequently replaced.

In another method, a bristle carrier surface with holes is provided and U-shaped tufts can enter and exit a pair of adjacent holes. Since the tufts are connected across the bottom, dislodging same is less easy than in a straight, blind hole.

As mentioned above, the bite plate itself can serve as the carrier, tufts protruding directly from holes in the bite plate. However, due to the 3D complexity of the bite plate, it is expected that the bite plate will be made, and then a carrier with bristles attached thereto added to the inner surfaces of the bite plate. This allows the carrier and bristles to be more easily manufactured, since the carrier is essentially planar.

Alternatively, as 3D printing becomes more sophisticated and less expensive, it may be possible to 3D print the entire device or the bite plate component or the carrier and bristle component thereof. The BLIZZIDENT® product claims to be a 3D printed toothbrush, but it appears that only the bite plate core is 3D printed, and that bristles are added in a separate manufacturing step. Although no manufacturing information is available, it appears that the tufts are inserted into holes or threaded through U-shaped conduits.

In yet another manufacturing method, single filaments are individually set into a carrier while the carrier is still hot, and carrier cooling sets the bristle in place. Usually the filaments are slightly larger at the bottom, further contributing to their fixation. Although more expensive a process, this method allows the most flexibility in brush head design as all the bristles can be of different lengths and stiffness. Such a manufacturing method would allow the making of a whole mouth toothbrush wherein the bristles are multidirectional and densely configured.

In yet another embodiment, and peel-and-stick bristle carrier covered with bristles on one side and adhesive on the other is provided. This may be an attractive low cost option that allows the existing bite plates to be used for cleaning as well. Further, the bristles can easily be replaced since bristles typically have a limited usage lifespan, which is expected to be less than the lifespan of a bite plate.

Bristles are preferably 2-15 mm in height, e.g., 5-12 mm or 7-10 mm, such that they can reach past the braces to the teeth and optionally to the gums. Typical filaments are 0.15 mm to 0.4 mm diameter, however, since the brush is specifically for brace use, it is possible to step outside these ranges. Shorter, stiffer and/or more dense bristles (e.g., 0-2 mm in length, 0.2-0.6 mm diameter) are used on occlusal surfaces, or the occlusal bristles can be omitted. Preferably, multiple bristle heights, angles and stiffness's are provided for cleaning the various surfaces.

Usually bristles are made of nylon, but other materials can be used. Nylon-polyester blend bristles or natural bristles are sometimes used. Bristles generally should have a flexural modulus of 2500 MPa or lower measured according to ISO 178:2001, a tensile modulus of 2600 MPa or lower, and an elongation at break % of 20% or lower, measured respectively according to ISO527-2: 1993.

The American Dental Association (ADA) provides specifications for manual and powered toothbrushes that must be followed for ADA Acceptance. Such standards are not wholly applicable to the device described herein, and it is likely that new standards would have to be developed for such a device. However, they do provide a useful starting point for bristles stiffness, density, and layout. The specifications given by ADA are as follows:

---
Brushing surface = 1-1.25 inches long (25.4 35.8 mm)
5/16-3/8 inches wide (7.9-9.5 mm)
2-4 rows of bristles
5-12 tufts per row
80-86 bristles per tuft
Diameter of commonly used bristles are:

Soft = 0.007 inch (0.2 mm)
Medium = 0.012 inch (0.3 mm)
Hard = 0.014 inch (0.4 mm)

---

In relation to bristle stiffness, reference should be made to the test methods in ANSI/ADA Standard No. 119-2008. See also ANSI/ADA Standard No. 120 for Powered Toothbrushes. Each incorporated by reference in its entirety for all purposes.

One bristle material is (a) 65-95 wt. % of at least a polytrimethylene terephthalate, and (b) 5-35 wt. % of at least a copolyether-ester having a Shore Hardness of 55 or higher measured according to IS0868, and described in WO2012088250. Others may prefer a softer bristle, e.g. 25-40 Shore A.

The bristle tufts can be flared before or after insertion, providing the multidirectional bristles. Alternatively, they can be inserted into the carrier at angles. Bristles and/or tufts of bristles can be arranged in repeated rows, staggered rows, circular or hexagonal patterns, zigzags, or any other desirable pattern. Various shapes are possible, including cylinders with pointed, flat or rounded tops, polygonal pillars with rounded tops, cones, boxes, as well as any combinations thereof.

By "multidirectional" bristles, what is meant is that the bristles protrude from the bite plate surfaces at 3 angles or more of about perpendicular and about +/−15° or +/−30° or +/−45° from perpendicular.

The meaning of "tufts" as used herein means a plurality of bristles are set in a particular hole or location. A tuft is composed of individual "bristles," and bristles can either be individually set or set in tufts.

By "U-shaped" what is meant herein is that the bite plates follow the curvature of the dentition, e.g., the biting surfaces of the teeth are in a substantially U-shaped curvature.

By "Euro arch" or "Euro form" herein what is meant is a dentition that narrows from the molars to the incisors. In contrast, other arch forms may be much rounder, or even having parallel sides, and not begin to narrow until closer to the front of the dentition.

When we refer to contacting "the teeth" or similar phrase herein, what is meant is the entire dentition, e.g., the teeth of both arches. If less than the entire dentition is intended, it will be referred to as maxillary teeth, mandibular teeth, or a "portion" of the teeth or specific teeth or arches will be identified by name or only a "portion" of the teeth will be referred to. Nevertheless, the bite plate need not contact every single tooth, since by definition some malocclusions may results in one or more teeth considerably out of alignment.

When we refer to contacting "occlusal and facial surfaces of the teeth," what is meant is that all teeth are intended to be contacted, allowing of course for badly misaligned teeth, which cannot be reached early in treatment. The phrase also allows some leeway at the molars to accommodate the fact that molars erupt over 20-25 years of age, if at all, or are removed to provide additional space for the remaining teeth, and thus most patients will not have a full set of adult teeth. Therefore, a bite plate intended to contact all teeth of the average patient, may not reach the molars of older patients, or patients with more mature dentition.

By "treatment modality" what is meant is a mode of action that causes an orthodontic benefit.

By "treatment modality source," what is meant is a device or component of a device that provides the treatment modality. For example, vibration is an orthodontic treatment modality and a vibratory source provides vibration. A vibratory source could also be called a vibrator. Another treatment modality is infrared or ultraviolet light, and an LED or laser could be an exemplary light source.

By "daily" use what is meant herein is use at least 67% of the days, since 67% compliance was enough to achieve an average of 50% faster tooth movement. Better compliance is expected to further improve results.

An "extraoral driver" is the extraoral component that provides the treatment modality, and in preferred embodiments is a housing having an e.g., a treatment modality source such as a vibrator or laser, a processor, a battery or other power source, and the wiring and processor needed to operate same, and wherein the housing has a socket for receiving the connector of the bite plate. The housing will preferably be water resistant or waterproof.

By "textured" herein in reference to the polymeric coating or covering, what is meant is that the polymer has sufficient texture as to provide a massaging or acupressure effect to the gums. Preferred textures include the use of "fingers" or other "protrusions" that are at least as tall as wide, and preferably twice as tall as wide (H≥2×W). Other textures include bristles, which are significantly taller than wide (e.g., about H≥5-10×W). Such fingers, protrusions can be arranged in any fashion, but are preferably separated from each other by at least the width of a protrusion so as to allow some motion to be imparted thereto under the influence of vibration. In such cases, the fingers should be made of a flexible material that is sufficiently soft as to accommodate such motion without breakage. Bristles, however, can be placed closer together, as their thinness allows sufficient flex.

By "braces" herein, we intend a broad usage including any fixed orthodontic appliance attached to the teeth or bone, not just traditional brackets and archwires.

By "cleaning braces" herein, we mean cleaning the braces and that part of the tooth adjacent the braces that is normally difficult to clean due to steric hindrance from the braces.

Since the textured surface may need to be softer than the remaining coating, the bite plate can comprise three layers— the stiff inner core, the coating, and a layer of softer material to create the textured surface. Additionally, a layer of bristles can be added that is of stiffer resin.

Massaging protrusions are preferably at least 2 mm in height, e.g., 2-7 mm, such that they can reach the gums, even when used with traditional orthodontic braces. Massaging fingers or pillars can be at least 1 mm in width, e.g., 1-2 mm, and separated by at least the same amount, e.g., separated by 1-2 or 2-4 mm. Bristles can be in the same height range (except occlusal bristles which are typically shorter), but correspondingly thinner, and placed closer together.

Protrusions can be arranged in repeated rows, staggered rows, circular or hexagonal patterns, or any other desirable pattern. Various shapes protrusions are possible, including cylinders with pointed, flat or rounded tops, polygonal pillars with rounded tops, cones, boxes, and very elongated shapes, such as ridges, wavy ridges and the like, as well as any combinations thereof.

The fingers can be made via injection molding, as such is easily achievable. Bristles can also be injection molded, but there is a lower limit on the fineness that can be achieved with current materials. Thus, bristles can be a separate material added, e.g., with staples, adhesives or melt adhered, and the like.

FIG. 9 shows standard tooth anatomy and terminology that will be used in the present disclosure.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated. When used in the context of part dimensions the term "about" includes that degree of tolerance that still allows the parts to operably connect, and thus will vary somewhat based on the flexibility of the material used for the part.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term "consisting essentially of" excludes only material elements that change the nature of the invention.

BRIEF DESCRIPTION OF THE DRAWINGS

FIG. 4A-D shows the inner core and connector parts, as well as various dimensions of the preferred connector.

FIG. 9 shows standard tooth anatomy and terminology used herein.

DETAILED DESCRIPTION

Figure 1A:
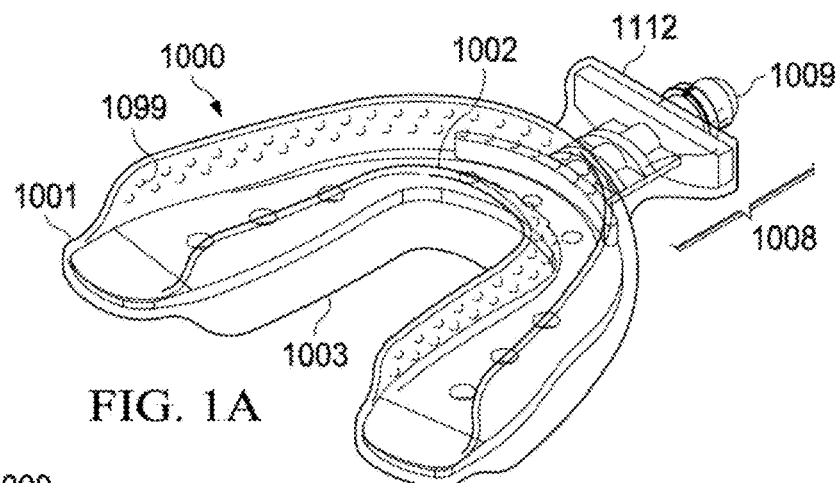
FIGS. 1A and 1B show a perspective view of a bite plate from two different angles.

The disclosure describes a massaging and/or brushing bite plate, preferably having the characteristics of the special prior art bite plates described in US2008227046, US2008227047, US2010055634, US20120322018, 61/624, 242, 61/615,480 and 61/673,236 and intended to be used with intra-oral or extra-oral vibratory or other treatment modality sources, as described in the preceding applications for patent, each incorporated by reference in their entireties.

In some embodiments, a bite plate for an orthodontic remodeling device is provided, said bite plate having a bristled and/or massaging surface and a connector for reversible connection to an extraoral driver. Another embodiment is the bite plate and driver together, preferably a vibratory driver, and yet another embodiment is a method of using such device wherein a patient wearing an orthodontic appliance bites the bite plate, applies vibration for 20 daily and such use speeds orthodontic remodeling by 50%.

In yet other embodiments, the devices herein described can use other treatment modalities in place of or in addition to pulsed or cyclic forces (aka vibration). Thus, the device can be fitted with IR light source, EM field source, microelectronic pulse source, and the like. However, in preferred modalities, the device includes a vibrational source, since vibration has already been proven in clinical trials to reduce remodeling time by 50%.

In yet other embodiments, the bite plate has fitted therein one or more e.g., coin vibrators or other tiny vibratory source(s), which is operably coupled to one or more coin battery(s) or charged capacitor(s), which are operably coupled to an optional processor for controlling the device and monitoring usage compliance. Thus, the entire device is intra-oral and of customizable fit.

In yet another embodiment, peel and stick embodiment is provided, wherein the peel and stick applique has either the textured surface or the bristles or both.

When the device is intended for use without braces, all of the gums can be in contact with the bite plate, but when intended for use with e.g., a class II or III corrector, the device may only contact incisors and cuspids on the facial side, as the corrector occupies space distal to this. Alternatively, the shape of the bite plate can be changed to accommodate correctors, and the fingers or bristles lengthened in this area.

The extraoral vibrator comprises at least a waterproof housing containing a vibrating motor operably coupled to a power source and an activation switch. In preferred embodiments, the housing also contains a processor to control the vibrating motor and to capture and transmit usage data to another device or monitoring parent or clinician. As noted above, other treatment modalities can be contained within the housing in addition to or in place of the vibrator.

The invention comprises one or more of the following embodiments, in any combination:

---

An orthodontic remodeling device comprising a bite plate reversibly coupled to an extraoral driver, said bite plate comprising:

(a) a stiff inner core that is substantially U-shaped to follow the curvature of a dental arch;
(b) a flexible biocompatible covering on said inner core;
(c) said flexible biocompatible covering shaped to contact at least the upper and lower incisors and cuspids and adjacent gums;
(d) wherein said inner core has a vibrator on a surface thereon operably coupled to a battery or charge capacitor and wherein said vibrator and battery or charged capacitor are hermetically sealed;
(e) said flexible biocompatible covering being a) textured on all gum facing surfaces thereof, so as to massage gums while in use or b) having multidirectional bristles on brace facing surfaces thereof and either no bristles or shorter and stiffer bristles on occlusal facing surfaces thereof, or both a and b;
said extraoral driver comprising:
(f) a housing containing a vibratory source operably coupled to a power source operably coupled to a processor; and
(g) wherein said vibratory source vibrates at a frequency between 1-400 Hz and at a force between 0.10-0.4 Newtons, preferably at 30 Hz and about 0.2N A intra-oral orthodontic remodeling device comprising a vibrating bite plate, said bite plate comprising:

(a) a stiff inner core that is substantially U-shaped to follow the curvature of a dental arch;
(b) a flexible biocompatible covering on said inner core;
(c) said flexible biocompatible covering shaped to contact at least the upper and lower incisors and cuspids and adjacent gums;
(d) wherein said inner core has a vibrator on a surface thereon operably coupled to a battery or charge capacitor and wherein said vibrator and battery or charged capacitor are hermetically sealed by said flexible biocompatible covering;
(e) said flexible biocompatible covering being i) textured on all gum facing surfaces thereof, so as to massage gums while in use or ii) having multidirectional bristles on brace facing surfaces thereof and either no bristles or shorter and stiffer bristles on occlusal facing surfaces thereof, or both i and ii.

A bite plate for an orthodontic remodeling device, said bite plate comprising:

(a) a bite plate that is U-shaped to follow the curvature of a dental arch;
(b) said bite plate having an outside edge having upper and lower rims to contact at least a portion of upper and lower facial surfaces of teeth and gums;
(c) said bite plate having an inside edge having upper and lower rims to contact at least a portion of an upper and lower lingual surfaces of teeth and gums;
(d) said upper and lower rims being textured on at least a portion of gum facing surfaces thereof, so as to massage gums while in use;

(e) wherein the bite plate has a connector on a midline thereof for reversibly coupling to an extra-oral orthodontic remodeling device that speeds tooth movement when used together with said bite plate, as compared to an orthodontic patient not using said device and bite plate.

A bite plate for an orthodontic remodeling device, said bite plate comprising:

(a) a bite plate that is U-shaped to follow the curvature of a dental arch;
(b) said bite having an outside edge having upper and lower rims to contact at least a portion of upper and lower facial surfaces of teeth;
(c) said bite plate having an inside edge having upper and lower rims to contact at least a portion of an upper and lower lingual surfaces of teeth;
(d) said upper and lower rims having multidirectional bristles on brace facing surfaces thereof, so as to clean braces while in use, and either: a) shorter and stiffer bristles on occlusal contacting surfaces or b) no bristles on occlusal contacting surfaces;
(e) wherein said bite plate has a connector on a midline thereof for reversibly coupling to an extra-oral orthodontic remodeling device that speeds tooth movement when used together with said bite plate, as compared to an orthodontic patient not using said device and bite plate.

A bite plate, said textured surfaces comprise spaced finger-like projections or spaced ridges or spaced wavy ridges A bite plate, said upper and lower rims have bristles on brace facing surfaces of said bite plate.

A bite plate having shorter and stiffer bristles on all occlusal contacting surfaces of said bite plate.

A bite plate lacking bristles on all occlusal contacting surfaces of said bite plate.

A bite plate lacking bristles on premolar and molar occlusal contacting surfaces of said bite plate.

A bite plate wherein said brace facing surfaces are recessed, providing a protruding edge to contact occlusal edges of vertical surfaces of teeth.

A bite plate wherein brace facing bristles have at least upper and lower tufts, said upper tufts angled downwards towards braces and said lower tufts angled upward toward braces.

A bite plate further comprising a middle tuft between said upper and lower tufts, said middle tuft being equally angled about a central point.

A bite plate wherein said bristles having a longer length to reach teeth surfaces, and a shorter length to reach brace surfaces.

A bite plate wherein said brace facing surfaces are recessed, providing a protruding edge to contact occlusal edges of vertical surfaces of teeth.

A bite plate said upper and lower rims being textured on gum facing surfaces thereof, so as to massage gums while in use, preferably said textured surfaces comprise spaced finger-like projections.

Said textured surface comprising finger-like projections being 0.5-5 mm in length and spaced 0.5-5 mm apart.

A peel-and-stick bristled applique comprising:

(a) a resin applique that is rectangular or U shaped and having assize and shape to fit a bite plate,
(b) said applique having a top surface and a bottom surface,
(c) said top surface having multidirectional bristles thereon, said bristles being of a size and shape for cleaning teeth and braces,
(d) said bottom surface being coated with adhesive, and
(e) said adhesive optionally covered with a removable protective layer.

A method of orthodontic remodeling comprising an orthodontic patient wearing an orthodontic appliance biting the bite plate and vibrating said bite plate for about 20 minutes, wherein daily use will speed orthodontic remodeling by 50%.

Figure 1B:
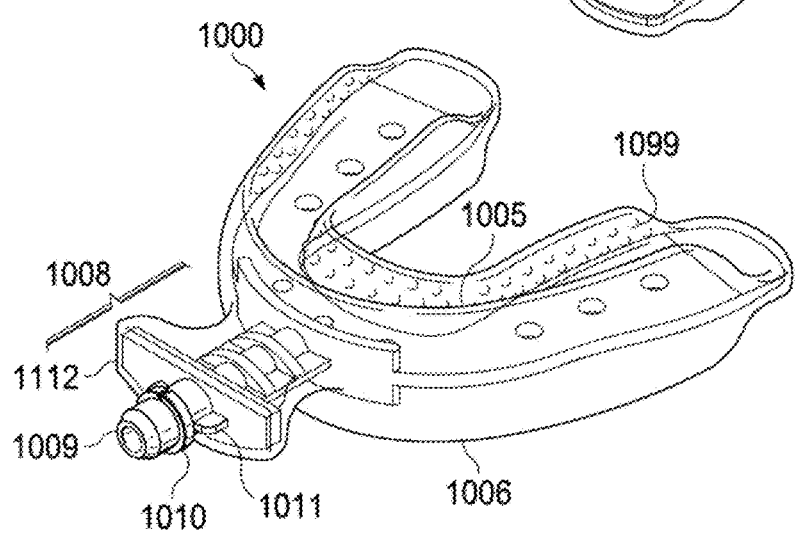
Figure 1C:
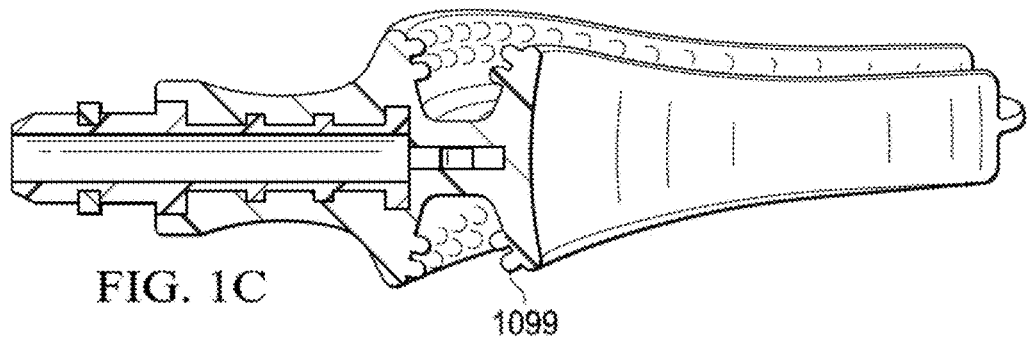
FIG. 1C shows a cross section of half a bite plate, more clearly illustrating the massaging projections, which are shown enlarged here for clarity.

FIG. 1A-C shows a bite plate (1000) from two angles in FIGS. 1A-B, as well as a cross sectional view (FIG. 1C) showing half a bite plate. Here the bite plate has a generally U-shaped base (1001) that contacts occlusal surfaces of the teeth, the bite plate having front (outer edge of the U) and back (inner edge of the U) edges, one or both edges having a rim to contact the facial and lingual surfaces of teeth and gums. Thus, upper lingual rim (1002), lower lingual rim (1003), upper facial rim (1005) and lower facial rim (1006) are shown. Textured surface (1099) are provided on at least those portions of the rims that contact the gums, thus providing a massaging or acupressure effect. Bristles (not shown) can be positioned below the nubby fingers that are shown on the textured surface (1099).

Also shown is the stem (1008), which is the portion of the bite plate (1000) that mates with a corresponding socket in the extra-oral housing (not shown here), which contains the power source, vibratory source or other treatment modality source, processor for controlling the device and providing optional compliance features.

In more detail, a cylindrical shaft (1009) is shown, having a groove into which a jump ring (1010) fits, and mates with a corresponding depression in the socket. Optional flare (1112) is also shown, and is configured to provide an appropriate surface so that the user can push the stem into the socket.

Figure 2:
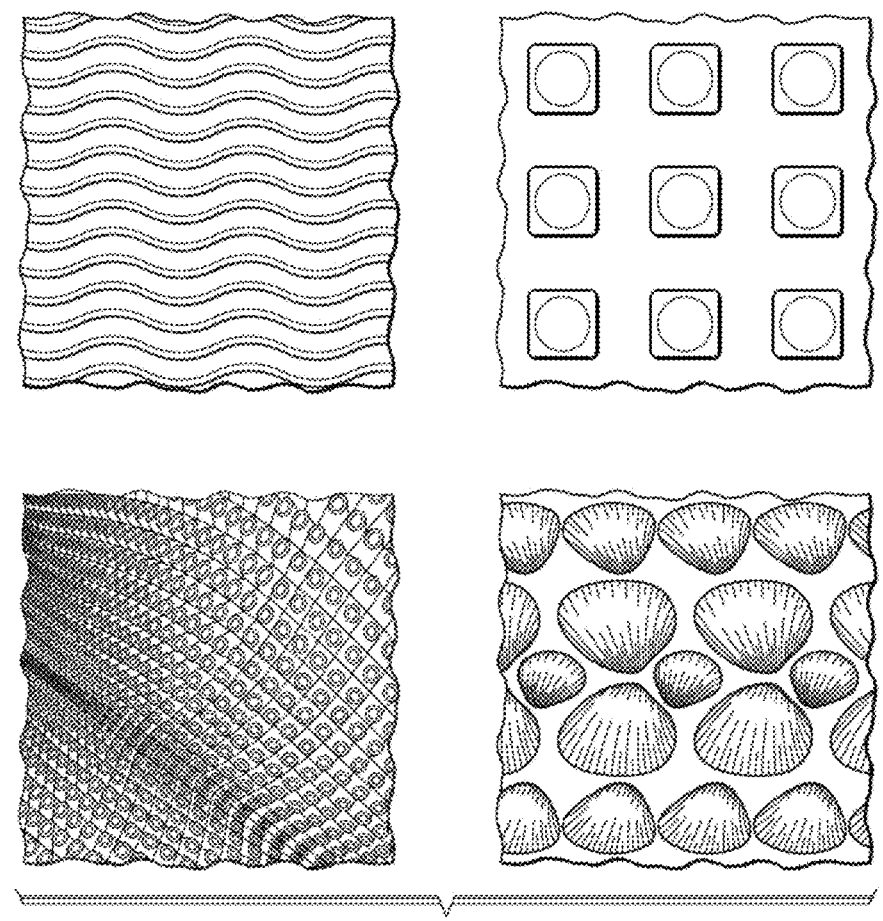
FIG. 2 shows a variety of projections (textured surface) from a top view.

FIG. 1C shows a cross section view of the bite plate, more clearly illustrating the textured surface (1099), as well as the inner core and outer coating components of the bite plate. The textured surface (1099) in FIG. 1C shows cylindrical pillars (not to scale), which can be with or without rounded or pointed tips (rounded shown), but any shaped textured design can be used, including wavy or straight lines, squares, triangles, pentagons, hexagons, arbitrary shapes like clam shells, polygonal pillars with semispherical tops, and the like, some of which are as shown in FIG. 2.

Figure 1D:
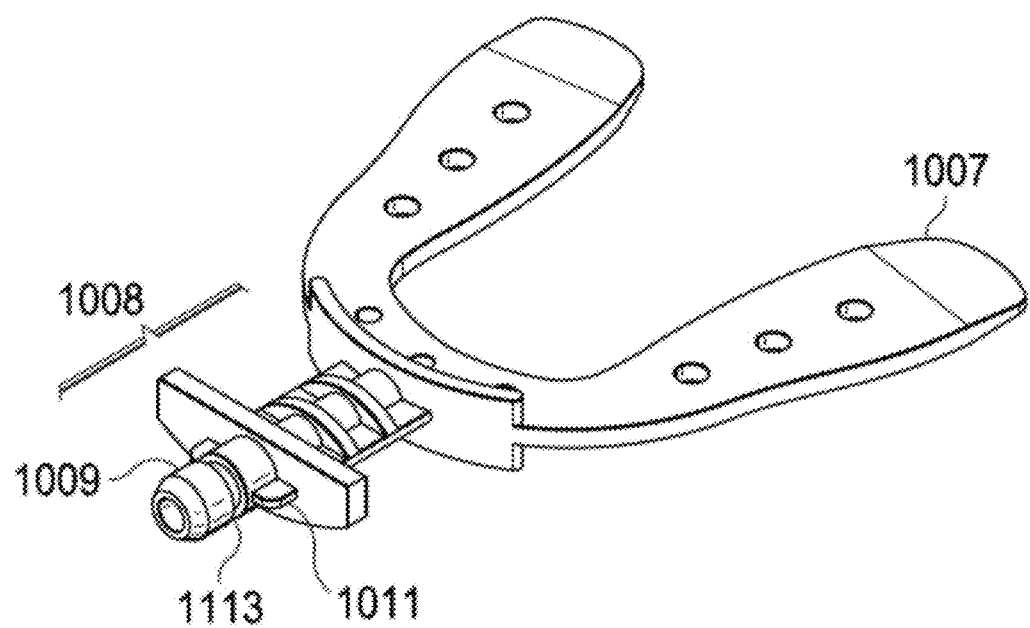
FIG. 1D shows the core of the bite plate, designed to fit the existing AcceleDent® device.

FIG. 1D shows just the inner core (1007) of the bite plate, typically made from a resin, metal or ceramic having a harder durometer than the outer surface, and providing sufficient rigidity to the stem (1008) so as to allow it to lockingly fit into the socket of the extra-oral component of the device. Cylindrical shaft (1009) has a groove (1013), into which jump ring (1010) fits. Also seen are locking pins (1011) that can also function as orientation pins if asymmetric, to prevent the bite plate from being inserted upside down. Generally plastics of at least 40 Shore D were used for the core, but metals or ceramics could also be used.

A coating is provided over this core, and provides the final shape of the bite plate. Such coating should be a biocompatible soft polymer of 40-70 Shore A, and particularly preferred is a medical grade, clear silicone.

Figure 3:
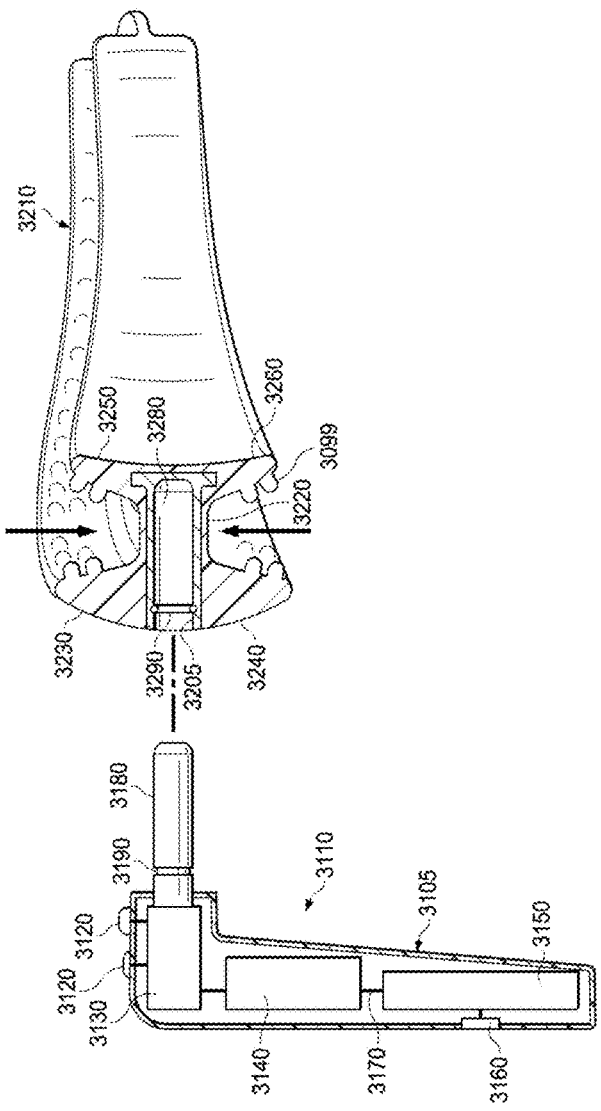
FIG. 3 shows a cutaway view of a device with extra-oral housing containing the treatment modality source and bite plate having a textured surface to massage/pressure the gums.

A complete device is more clearly illustrated in FIG. 3, which is a cross section of an orthodontic remodeling device (3110) and half of a bite plate (3210) with fingers (3099). The orthodontic remodeling device (3110) has a housing (3105) containing all components, except the stem (3180), which protrudes therefrom. Preferably, housing (3105) is water resistant or even more preferred it is waterproof or hermetically sealed. The housing contains battery (3130), preferably a rechargeable battery and can have an optional charging port (not shown).

The source of treatment modality (3140) is shown schematically as a simple box. If the device uses vibration as a treatment modality, this box would represent e.g., piezoelectric motors or an offset weight DC motor. However, as noted elsewhere herein, other modalities, such as electrical micropulses, heat, IR, can be used in place of or in addition to the vibrational modality.

Processor (3150) captures usage data, and may control the treatment modality source (3140). Data is transmitted to a server or computer or the Internet via data port or USB (3160). Connections or wires (3170) are shown in simple form only and not intended to convey actual wiring connections, as are on/off switches (3120). Stem (3180) is shown here with depressions (3190), which can circumnavigate the stem in one embodiment, but many variations of snap fitting and other connectors are possible.

Bite plate (3210) has a hard inner core that forms the socket (3205) and can be any suitable shape. A circle spring (3290) fits into depressions (3190) on stem (3180) and thus removably snap fits onto the extraoral orthodontic driver. The bite plate has the labial, lingual edges and occlusal surface as already described, and fitted with textured surface (3099). Thus (3220) is the flat surface that contacts occlusal surfaces of the teeth, edges (3230) and (3240) contact the facial tooth and gum surfaces, while edges (3250) and (3260) contact the lingual tooth and gum surfaces.

These various surfaces, (3220), (3230), (3240), (3250) and (3260) have the textured surfaces (3099) thereon to provide massaging or acupressure effect when in use. Preferably, these edges are made of a resilient material of durometer 40-70 Shore A, most preferred is a biocompatible or medical grade clear silicone. Where acupressure is intended, the material can be stiffer, and where massage intended the material can be softer.

In the device of FIG. 3, the bite plate has a socket, and the driver has the plug or stem that fits into the socket, but of course these can be reversed.

Preferably, the connector is identical to that found on the AcceleDent® and AcceleDent-Aura™ and is shown in detail in FIG. 4A-D. Using similar connectors allows the bite plates to be interchangeable, and also allows any bite plate inventory to be used even when the driver unit model is updated. Thus, these sizes are valuable for interchangeability of parts. The minimum for interchangeable parts requires the cylindrical post of at least 10.25 mm in length× 6.35 mm in diameter (tolerance noted to be +0.03, −0.1) mm with a groove 4 mm from the attached end of the post.

The connector has a flared base (flare not shown herein because made from the overcoating material, but can be seen in FIG. 1) with a flat surface opposite the bite plate, from which protrudes a centrally positioned cylindrical post that is 6-7 (6.35+0.03, −0.1) mm in diameter, 10-11 (10.25) mm in length, and having a groove circumventing the post about half way (4 mm from flat surface, with width of 1.65 mm, depth of 6.35-5.5=0.85).

The flared base is somewhat dumbbell shaped in cross section, thus providing a convenient thumb/finger engagement surface for pressing the bite plate connector into the corresponding socket of the driver. However, this feature is not essential for interchangeability and can be omitted.

The bottom of the post also has a pair of ~1.4×3 mm pins projecting 180° from each other (in the same plane as the occlusal contacting base of the bite plate). These pins have a total spread of 11.30 mm at the topmost edge, but flare 10° on each side (20° total) to reach the flat surface of the base. The pins are 1.63 mm thick, and 2.75 mm high. The pins are optional, and a connector will still fit into the same driver.

The base of the connector also preferably has a pair of recessions ~1.5 mm wide×3 mm long×2 mm deep (1.58× 3.27×2.5 mm) on the flat surface thereof for engaging clips from the driver, the recessions being about 16-17 mm apart (22.89 mm in spread), and positioned right below the pins. The recessions can be omitted however, if the base is either not flared or is otherwise smaller, such that the remaining post and pins still fit, leaving the engaging clips on the driver free. These dimensions are approximate, and exact dimensions are provided on FIG. 4, although some tolerance of dimensions can be accommodated and still fit, as indicated in the claim language by use of the word "about".

Figure 5A:
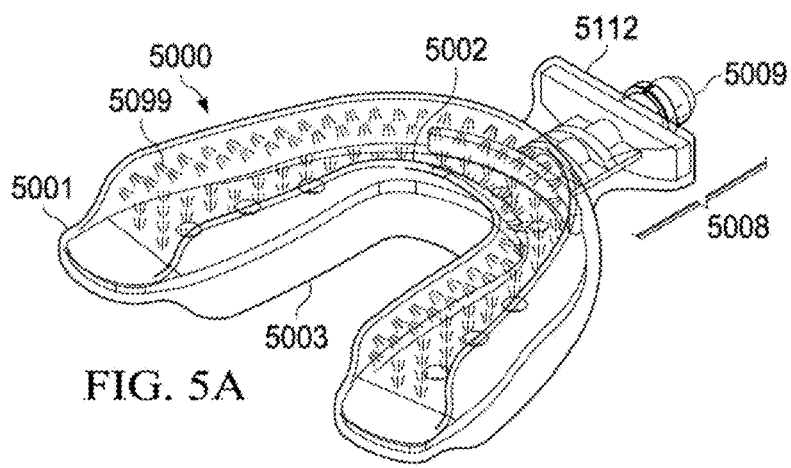
FIGS. 5A and 5B show a perspective view of a bite plate from two different angles.
Figure 5B:
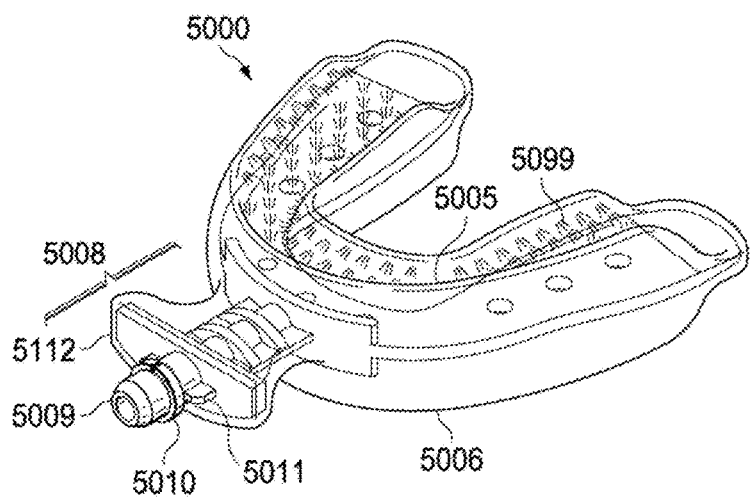
Figure 5C:
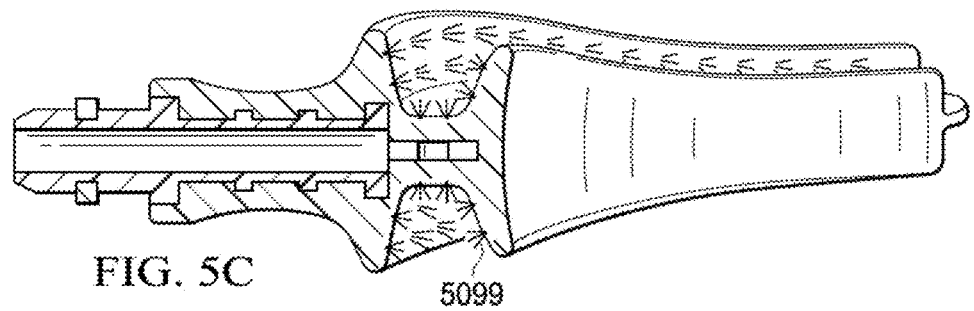
FIG. 5C shows a cross section of half a bite plate, more clearly illustrating the bristles, which are shown simplified herein for clarity.

FIG. 5A-C shows a bite plate (5000) from two angles (FIGS. 5A-B), as well as a cross sectional view (FIG. 5C) showing half a bite plate. Here the bite plate has a generally U-shaped base (5001) that contacts occlusal surfaces of teeth, the bite plate having front (outer edge of the U) and back (inner edge of the U) edges, one or both edges having a rim to contact the facial and lingual surfaces of teeth and gums. Thus, upper lingual rim (5002), lower lingual rim (5003), upper facial rim (5005) and lower facial rim (5006) are shown. Bristles (5099) are provided on at least at those portions of the rims that contact the teeth and gums, thus providing a cleaning effect. Bristles (5099) are simplified for ease of viewing and are positioned on the teeth facing surfaces of the bite plate. The bristles can be on facial vertical teeth contacting surfaces since this is where many fixed appliances are positions, on lingual and facial vertical surfaces, or on all teeth contacting surfaces, including occlusal surfaces.

Also shown is the stem (5008), which is the portion of the bite plate (5000) that mates with a corresponding socket in the extra-oral housing (not shown here), which contains the power source, vibratory source or other treatment modality source, processor for controlling the device and providing optional compliance features.

In more detail, a cylindrical shaft (5009) is shown, having a groove into which a jump ring (5010) fits, and mates with a corresponding depression in the socket. Optional flare (5112) is also shown, and is configured to provide an appropriate surface so that the user can push the stem into the socket.

FIG. 5C shows a cross section view of the bite plate, more clearly illustrating the inner bristled surfaces (5099), as well as the inner core and outer coating components of the bite plate. The bristles (5099) in FIG. 5C shown are cylindrical pillars (not drawn to scale), which can be with or without rounded, pointed or angled tips, but any shaped bristle can be used.

Figure 6A:
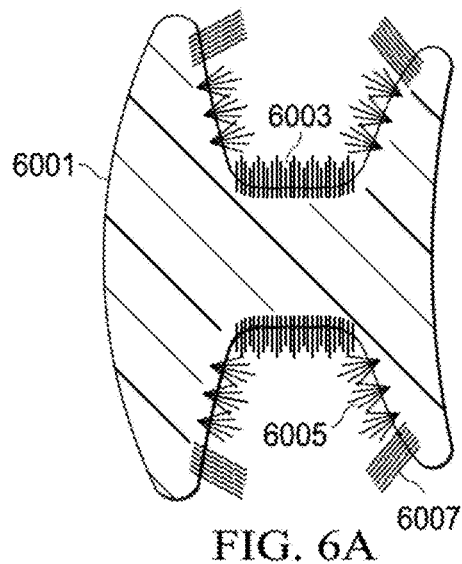
FIG. 6A-D show a variety of bristle patterns.
Figure 6B:
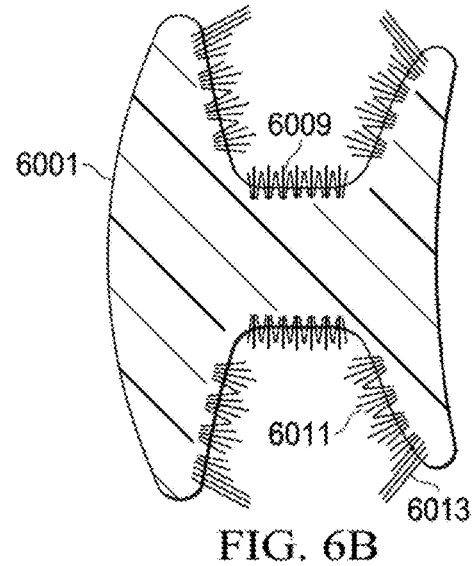
Figure 6C:
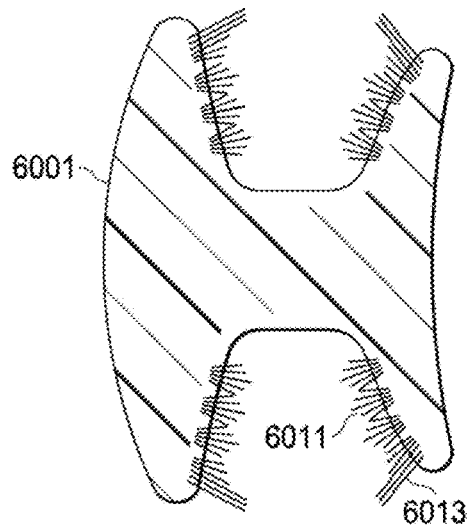

The bite plate (6001) in FIG. 6A is shown in cross section with bristles (6003, 6005 and 6007) shown. As can be seen, gum contacting bristles (6007) can be longer than brace contacting bristles (6005), as well as angled to penetrate under the gum line. Another pattern is shown in FIG. 6B where bite plate (6001) has bristles (6009) for cleaning occlusal surfaces of teeth. The bristles in this area can be any known in the toothbrush art, and one simple pattern is shown, but such bristles may be shorter and or stiffer (or omitted entirely), such that vibration can be effectively conveyed or teeth and bone. Brace contacting bristles (6011) are mounted at a variety of angles and set at different lengths, to penetrate and clean both the braces, as well as the tooth surface immediately adjacent the braces. As before, gum contacting bristles (6013) are longer and angled to clean the gum and gingiva. FIG. 6C shows an embodiment where occlusal bristles are shorter and thicker and with massaging projections on gum facing surfaces.

Figure 6D:
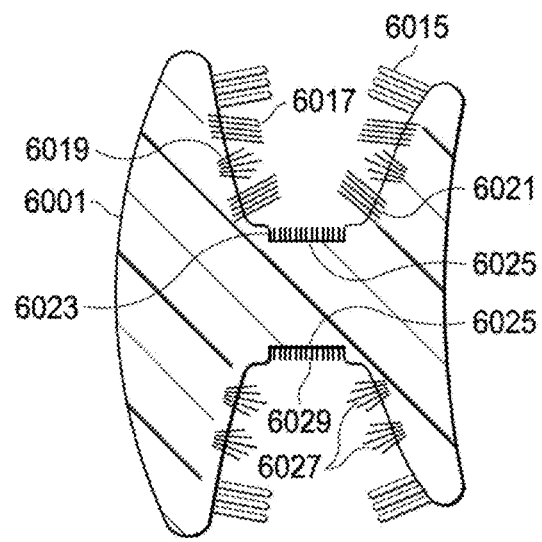

FIG. 6D shows an embodiment designed to massage gums, clean braces, and yet still allow vibration forces to be transferred to occlusal and vertical teeth surfaces. The bite plate (6001) has massaging fingers (6015) on gum facing surfaces. Downward angled bristles (6017), a central tuft (6019) and upwardly angled bristles (6021) are designed to reach to and clean the braces and teeth surfaces around the braces. The brace facing surfaces are recessed, providing a small edge (6023), which will contact the occlusal-edge of the vertical surfaces of the teeth. Very short stiff bristles (6029) together with the edge (6023) allow the transfer of vibration in the two axes, thus ensuring that the device does not lose clinical efficacy. This particular bite plate is designed for upper braces (facial or lingual) and thus the bottom bristles (6027) are simply tufted. If desired, only the upper facial surface can have the special brace cleaning bristles, and this can be reversed for lingual braces.

These patterns are exemplary only, and cleaning tests will elaborate on the optimal bristle pattern. Dental models equipped with braces will be coated with a colored polymeric solution to provide a testable coating for teeth cleaning experiments. Various bristle patterns will be made, and attached to an existing bite plate with adhesive, and the device will be activated for 20 minutes. Cleaning ability will be scored by reduction in weight of the model caused by removal of the polymeric coating, as well as photographically using software to score the amount of remaining color, e.g., blue or green.

Figure 7:
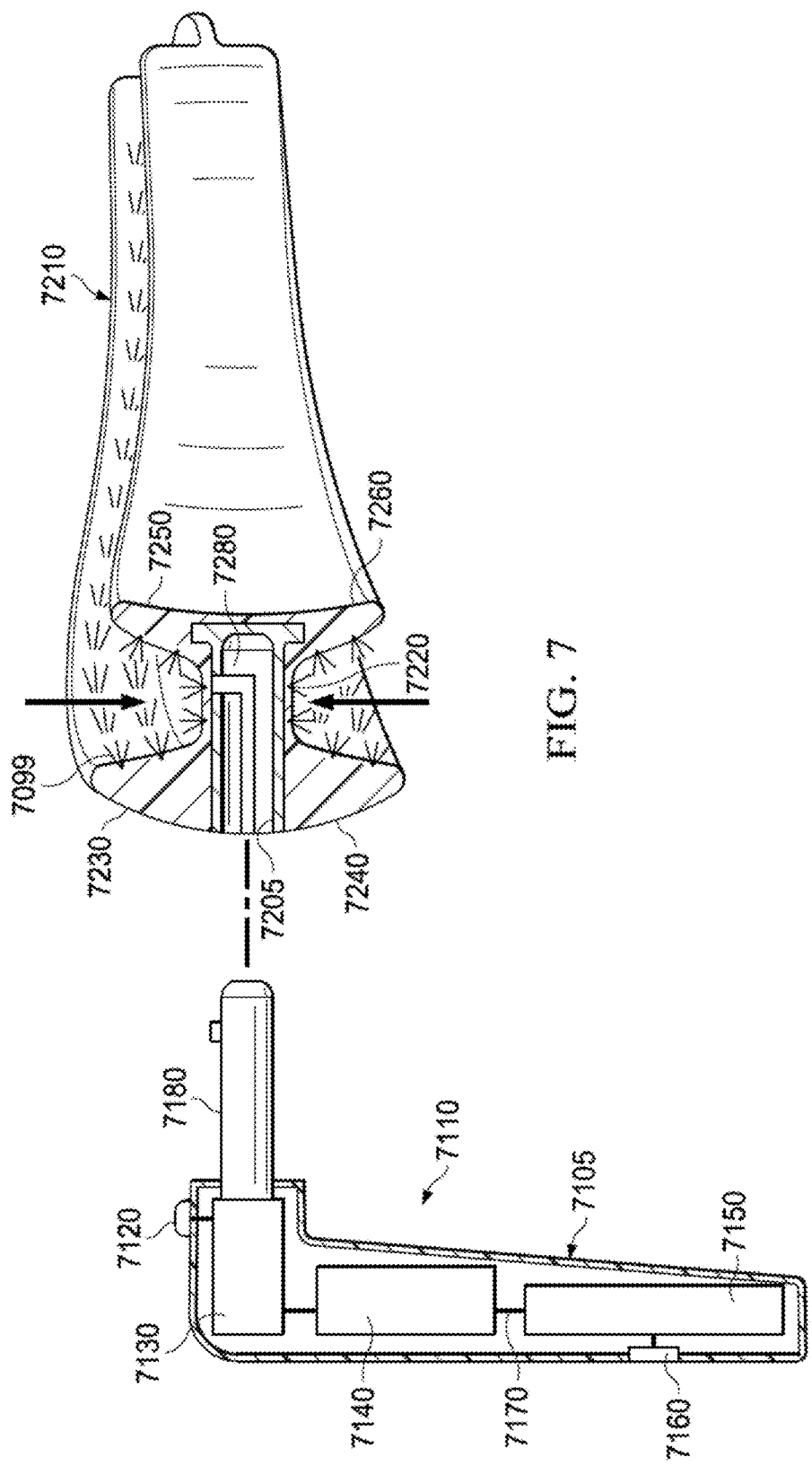
FIG. 7 shows a cutaway view of a device with extra-oral housing containing the treatment modality source and bite plate having a bristled surface to clean the braces or other fixed appliance, teeth and gums.

A complete device is more clearly illustrated in FIG. 7, which is a cross section of an orthodontic remodeling device (7110) and half of a bite plate (7210) with bristles (7099). The orthodontic remodeling device (7110) has a housing (7105) containing all components, except the stem (7180), which protrudes therefrom. Preferably, housing (7105) is water resistant or even more preferred it is waterproof or hermetically sealed. The housing contains battery (7130), preferably a rechargeable battery and can have an optional charging port (not shown).

The source of treatment modality (7140) is shown schematically as a simple box. The device uses vibration as a treatment modality since this device is intended for cleaning uses. Therefore, this box represents e.g., piezoelectric motors or an offset weight DC motor. However, as noted elsewhere herein, other modalities, such as electrical micropulses, heat, IR, can be used in addition to the vibrational modality.

Processor (7150) captures usage data and controls the treatment modality source (7140). Data is transmitted to a server or computer or the Internet via data port or USB (7160). Connections or wires (7170) are shown in simple form only and not intended to convey actual wiring connections, as are on/off switches (7120). Stem (7180) is shown here having a bayonet mount fitting into groove (7280) in the socket (7205), a half turn locking it in.

Bite plate (7210) has a hard inner core that forms the socket (7205) and can be any suitable shape. A circle spring or jump ring (7290) fits into depressions (7190) on stem (7180) and thus removably snap fits onto the extra-oral orthodontic driver. The bite plate has the labial, lingual edges or rims and occlusal surface as already described, and fitted with bristles (7099). Thus, (7220) is the flat surface that contacts occlusal surfaces of the teeth, edges or rims (7230) and (7240) contact the facial tooth and gum surfaces, while edges (7250) and (7260) contact the lingual tooth and gum surfaces.

These various surfaces, (7220, 7230, 7240, 7250 and 7260) have the bristles (7099) thereon to provide cleaning effect when in use. It can be seen that this device contacts all tooth surfaces of the entire dentition at the same time. Thus, teeth cleaning time is minimized and can coincide with vibrational use for orthodontic remodeling.

We have found that optimal orthodontic remodeling uses require less than 100 Hz, probably because time is needed for the biological sensors to reset so they can continue to respond to the cyclic forces. In fact the currently cleared device uses a 30 Hz frequency, and very low force of 0.2-0.25 Newtons (~20 grams). Electric toothbrushes, however, are said to be optimized at 260 Hz and 128 grams, while manual toothbrushes apply an average of twice that force. We predict, however, that because orthodontic remodeling times last for 20 minutes, instead of the 2 minutes recommended by e.g., Sonicare®, the extra time will more than make up for the less than optimized frequency and force. Further, if desired, the device can be quipped with two speeds, allowing 260 Hz for 2 minutes and then switching to the orthodontic frequencies, currently between 20-40 Hz. This can be accomplished by including a separate vibratory source, or providing a single source capable of more than one speed setting, the program being controlled by the processor. If this option is pursued, bristle stiffness will need to be corresponding lower, whereas a stiffer bristle can be used at the lower frequency and force.

Figure 8:
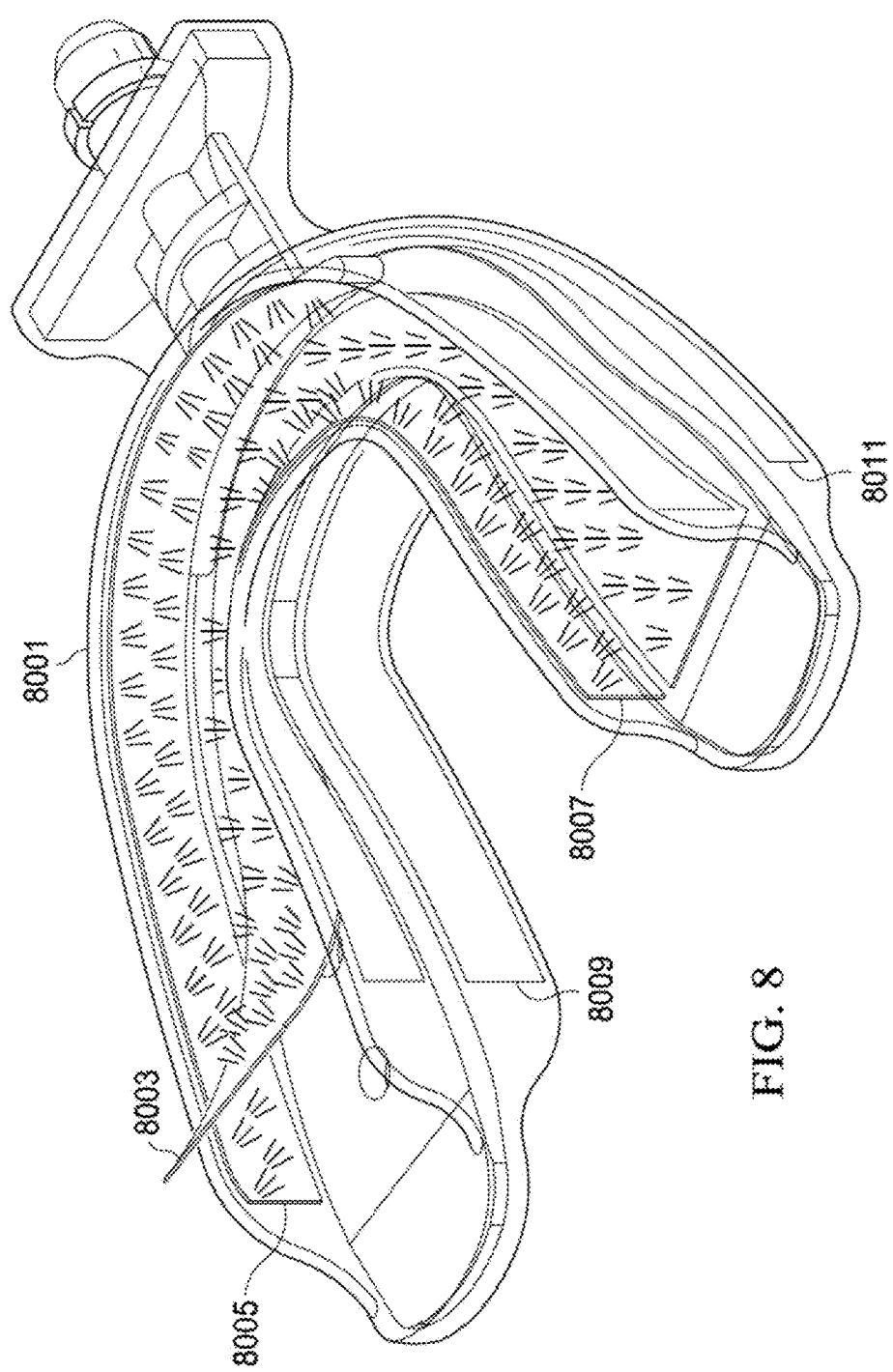
FIG. 8 shows a peel and stick bristle surface that can be applied to existing bite plates (see left side where peel and stick edge lifted from bite plate).

FIG. 8 shows a peel-and-stick bristled surface that can be used with existing bite plates and allows easy updating of the bristle surfaces, which are subject to wear and accumulation of bacteria. As many as 4 rectangular peel-and-stick strips (8005, 8007, 8009, 8011) can be peeled and stuck to vertical surfaces of the bite plate, and a pair of U-shaped stickers (8003) (only one seen from this angle) with shorter and/or stiffer bristles can be applied to occlusal surfaces or as noted above, omitted. Fewer stickers can be used if the patient e.g., only has a fixed appliances on a single arch, as is sometimes the case. If desired, the peel and stick strip can be equipped with an occlusal edge corresponding to edge 3023 (not shown) for contacting the occlusal edge of the vertical teeth surfaces.

The following are incorporated by reference here in their entireties.

US2008227046, US2008227047, US2010055634, US20120322018, US2013059263, 61/624,242, 61/615,480 and 61/673,236, 61/769,507, 60/906,807.

61/837,021, titled MASSAGING BITE PLATE, filed on Jun. 19, 2013.

61/911,355, titled BRUSHING BITE PLATE, filed on Dec. 3, 2013.

Kau, et al., The clinical evaluation of a novel cyclical force generating device in orthodontics, Orthodontic Practice 1(1) (2010).

DE19934117; U.S. Pat. No. 5,856,373; US20110200973; U.S. Pat. No. 5,017,626; U.S. Pat. No. 4,459,193; U.S. Pat. No. 4,411,625; U.S. Pat. No. 4,771,084; US20050049326.

U.S. Pat. No. 8,308,246; U.S. Pat. No. 6,988,777; U.S. Pat. No. 6,871,373; U.S. Pat. No. 6,869,148; U.S. Pat. No. 6,405,401; U.S. Pat. No. 6,341,824; U.S. Pat. No. 6,161,243; U.S. Pat. No. 5,926,904; U.S. Pat. No. 5,605,383; U.S. Pat. No. 5,542,749; U.S. Pat. No. 5,518,300; U.S. Pat. No. 5,325,560; U.S. Pat. No. 5,165,761; U.S. Pat. No. 4,372,004.

US20130192012; US20120317738; US20120090118; US20100043165.

WO2012088250

US20120260442

BLIZZIDENT (see blizzident.com).

While the invention is described above in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. An orthodontic remodeling device, comprising
(a) an extra-oral orthodontic remodeling driver that vibrates at a frequency between 1-400 Hz and a force between 0.1-0.5 Newtons operably coupled to a bite plate;
(b) said bite plate being U-shaped to follow the curvature of a dental arch;
(c) said bite plate having an outside edge having upper and lower rims to contact at least a portion of upper and lower facial surfaces of teeth and gums;
(d) said bite plate having an inside edge having upper and lower rims to contact at least a portion of an upper and lower lingual surfaces of teeth and gums;
(e) each of said upper and lower rims being i) textured on at least a portion of gum facing surfaces thereof, so as to massage gums while in use, or ii) bristled on at least brace facing surfaces thereof, so as to clean braces when in use, or iii) both i and ii;
(f) wherein the bite plate has a connector on a midline thereof for reversibly coupling to said extra-oral orthodontic remodeling driver;
(g) wherein daily use of said device speeds tooth movement, as compared to an orthodontic patient not using said device.

2. The device of claim 1, wherein said textured surfaces comprise spaced finger-like projections.

3. The device of claim 1, wherein said textured surfaces comprises spaced ridges.

4. The device of claim 1, wherein said textured surfaces comprises spaced wavy ridges.

5. The device of claim 1, further comprising bristles on all occlusal contacting surfaces of said bite plate which are shorter and stiffer than bristles on other surfaces of said bite plate.

6. The device of claim 1, lacking bristles on all occlusal contacting surfaces of said bite plate.

7. The device of claim 1, lacking bristles on at least some occlusal contacting surfaces of said bite plate.

8. The device of claim 1, wherein said brace facing surfaces are recessed, providing a protruding edge to contact occlusal edges of vertical surfaces of teeth.

9. The device of claim 1, wherein said brace facing bristles have at least upper and lower tufts, said upper tufts angled downwards towards braces and said lower tufts angled upward toward braces.

10. The device of claim 9, further comprising a middle tuft between said upper and lower tufts, said middle tuft being angled about a central point.

11. The device of claim 1, said bristles having a longer length to reach teeth surfaces, and a shorter length to reach brace surfaces.

12. The device of claim 1, wherein said textured surfaces comprise spaced finger-like projections of 2-5 mm in length spaced 0.5-2 mm apart.

13. An intra-oral orthodontic remodeling device comprising a vibrating bite plate that vibrates at a selected frequency between 1-400 Hz and a selected force between 0.1-0.5 Newtons, said bite plate comprising:
(a) a stiff inner core that is substantially U-shaped to follow the curvature of a dental arch;
(b) a flexible biocompatible covering on said inner core;
(c) said flexible biocompatible covering shaped to contact at least the upper and lower incisors and cuspids and adjacent gums;
(d) wherein said inner core has a vibrator on a surface thereon operably coupled to a battery or charge capacitor and wherein said vibrator and battery or charged capacitor are hermetically sealed by said flexible biocompatible covering;
(e) said flexible biocompatible covering being i) textured on all gum facing surfaces thereof, so as to massage gums while in use or ii) having multidirectional bristles on brace facing surfaces thereof and either no bristles or shorter and stiffer bristles on occlusal facing surfaces thereof, or both i and ii.

14. The intra-oral orthodontic remodeling device of claim 13, said textured surfaces comprising finger-like projections.

15. The intra-oral orthodontic remodeling device of claim 13, said textured surfaces comprising finger-like projections being 3-7 mm in length and spaced 0.5-2 mm apart.

16. The intra-oral orthodontic remodeling device of claim 13, some bristles having a longer length to reach teeth surfaces, and some bristles having a shorter length to reach brace surfaces.

17. The intra-oral orthodontic remodeling device of claim 13, wherein said brace facing surfaces are recessed, providing a protruding edge to contact occlusal edges of vertical surfaces of teeth.

18. The intra-oral orthodontic remodeling device of claim 13, wherein said brace facing bristles have at least upper and lower tufts, said upper tufts angled downwards towards braces and said lower tufts angled upward toward braces.

19. The intra-oral orthodontic remodeling device of claim 18, further comprising a middle tuft between said upper and lower tufts, said middle tuft being angled about a central point.

20. An orthodontic remodeling device, comprising:
(a) a bite plate reversibly coupled to an extraoral driver; said bite plate comprising:
(b) a stiff inner core that is substantially U-shaped to follow the curvature of a dental arch;
(c) a flexible biocompatible covering on said inner core;
(d) said flexible biocompatible covering shaped to contact at least the upper and lower incisors and cuspids and adjacent gums;
(e) said flexible biocompatible covering being a) textured on all gum facing surfaces thereof, so as to massage gums while in use or b) having multidirectional bristles on brace facing surfaces thereof and either no bristles or shorter and stiffer bristles on occlusal facing surfaces thereof, or both a and b;
said extraoral driver comprising:
(f) a housing containing a vibratory source operably coupled to a power source operably coupled to a processor; and
(g) wherein said vibratory source vibrates at a frequency between 1-400 Hz and at a force between 0.1-0.5 Newtons.

21. An orthodontic remodeling device, comprising:
a. an extra-oral orthodontic remodeling driver that vibrates at 20-40 Hz;
b. a bite plate being U-shaped to follow the curvature of a dental arch;
c. said bite plate having an outside edge having upper and lower rims to contact upper and lower facial surfaces of teeth and gums;
d. said upper and lower rims bristled on facial surfaces thereof, so as to clean braces when in use;
e. wherein the bite plate has a connector on a midline thereof for coupling to said extra-oral orthodontic remodeling driver;
f. wherein said device is adapted to be held only by an orthodontic patient biting said bite plate;
g. wherein said device speeds orthodontic remodeling as compared to an orthodontic patient not using said device; and
h. wherein said device provides improved brace cleaning as compared to an orthodontic patient not using said device, but only using a toothbrush for cleaning.

22. A method of orthodontic remodeling, comprising the steps of an orthodontic patient wearing an orthodontic appliance, biting a bite plate of an orthodontic remodeling device and vibrating said bite plate for about 20 minutes, wherein daily vibration will speed orthodontic remodeling by 50% as compared to a patient not using said vibration, and wherein said orthodontic remodeling device comprises:
(a) an extra-oral orthodontic remodeling driver that vibrates at vibrates at a frequency between 1-400 Hz and a force between 0.1-0.5 Newtons operably coupled to the bite plate;
(b) said bite plate being U-shaped to follow the curvature of a dental arch;
(c) said bite plate having an outside edge having upper and lower rims to contact at least a portion of upper and lower facial surfaces of teeth and gums;
(d) said bite plate having an inside edge having upper and lower rims to contact at least a portion of an upper and lower lingual surfaces of teeth and gums;
(e) each of said upper and lower rims being i) textured on at least a portion of gum facing surfaces thereof, so as to massage gums while in use, or ii) bristled on at least brace facing surfaces thereof, so as to clean braces when in use, or iii) both i and ii; and,
(f) wherein the bite plate has a connector on a midline thereof for reversibly coupling to said extra-oral orthodontic remodeling driver.

\* \* \* \* \*